US00PP35147P2

(12) United States Plant Patent
Lee

(10) Patent No.: US PP35,147 P2
(45) Date of Patent: May 2, 2023

(54) AZALEA PLANT NAMED 'LAZAMORWHI'

(50) Latin Name: ***Rhododendron* hybrid**
Varietal Denomination: 'Lazamorwhi'

(71) Applicant: Plant Development Services, Inc., Loxley, AL (US)

(72) Inventor: Robert Edward Lee, Independence, LA (US)

(73) Assignees: Robert Edward Lee, Independence, LA (US); Plant Development Services, Inc., Loxley, AL (US)

( * ) Notice: Subject to any disclaimer, the term of this patent is extended or adjusted under 35 U.S.C. 154(b) by 56 days.

(21) Appl. No.: 17/854,696

(22) Filed: Jun. 30, 2022

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 5/02
See application file for complete search history.

(56) References Cited

U.S. PATENT DOCUMENTS

PP10,581 P 9/1998 Lee
PP25,073 P3 11/2014 Johnson

OTHER PUBLICATIONS

"Woodies & Edibles" 2022 Catalog from Star® Roses and Plants.

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of Azalea plant, referred to by its cultivar name, 'Lazamorwhi', is disclosed. The new variety forms attractive, solid white-colored single inflorescences. Attractive medium-green colored foliage is formed, which contrasts beautifully with the flowers. A moderately vigorous, mounding, globose, upright growth habit is displayed. The new variety is well suited for providing attractive ornamentation in the landscape.

2 Drawing Sheets

Latin name of genus and species of plant claimed: *Rhododendron* hybrid.

Variety denomination: 'Lazamorwhi'.

STATEMENT REGARDING PRIOR DISCLOSURES BY THE INVENTOR

The first offer for sale of the new variety was presented in the non-enabling disclosure of 2022 Star® Roses and Plants Woodies & Edibles Catalog, which was released on Jul. 1, 2021. The first offer for sale of the new variety was by the inventor or another who obtained the new variety directly or indirectly from the inventor. No plants of the new variety have been sold in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The new variety of Azalea plant of the present invention was created by controlled breeding in Independence, La., during the spring of 1996 by artificial pollination wherein two parents were crossed which previously had been studied in the hope that they would contribute the desired characteristics. The objective of the breeding program was the development of new evergreen Azalea plants with multi-season blooming. The female parent (i.e., the seed parent) of the new variety was the 'Watchet' variety (not patented). The male parent (i.e., the pollen parent) of the new variety was the 'Conleb' variety (U.S. Plant Pat. No. 10,581).

The parentage of the new variety can be summarized as follows:

'Watchet' x 'Conleb'

The seeds resulting from the above pollination were sown and small plants were obtained which were physically and biologically different from each other. Selective study during the fall of 2002 resulted in the identification of a single plant of the new variety.

The new variety has been found to undergo asexual propagation in Independence, La. and Loxley, Ala. since Fall 2002 by a number of routes, including stem cuttings and softwood cuttings. Asexual propagation by the above-mentioned techniques in Independence, La. and Loxley, Ala. has shown that the characteristics of the new variety are stable and are strictly transmissible by asexual propagation from one generation to another. Accordingly, the new variety undergoes asexual propagation in a true-to-type manner.

BRIEF SUMMARY OF THE INVENTION

It was found that the new variety of rose plant of the present invention possesses the following combination of characteristics:

(a) forms solid, white colored single inflorescences,
(b) exhibits medium-green colored foliage, and (c) provides moderately vigorous, mounding, globose, upright growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Watchet' variety (i.e., the seed parent) forms moderate pink to white inflorescences with a greenish white throat, provides dark-green colored foliage, and exhibits an upright and spreading growth habit, whereas the new variety forms solid, white colored inflorescences, provides medium-green colored foliage, and exhibits a mounding, globose, and upright growth habit. In addition, the 'Conleb' variety (i.e., the pollen parent) forms orange to red colored inflorescences, whereas the new variety forms solid, white colored inflorescences and provides foliage that is lighter green colored compared to the 'Conleb' variety. Moreover, the new variety can be readily distinguished from other similar non-parental varieties. For example, the 'ROBLEX' variety (U.S. Plant Pat. No. 25,073) forms larger leaves that are spaced farther apart compared to the new variety.

The new variety has been named 'Lazamorwhi'.

BRIEF DESCRIPTION OF THE DRAWINGS

The accompanying photographs show as nearly true as it is reasonably possible to make the same, in a color illustration of this character, typical specimens of the plant parts of the new variety. The plants of the new variety were grown in 3-gallon containers for approximately one year in an outdoor nursery in Cochranville, Pa.

DETAILED BOTANICAL DESCRIPTION

Figure 1:
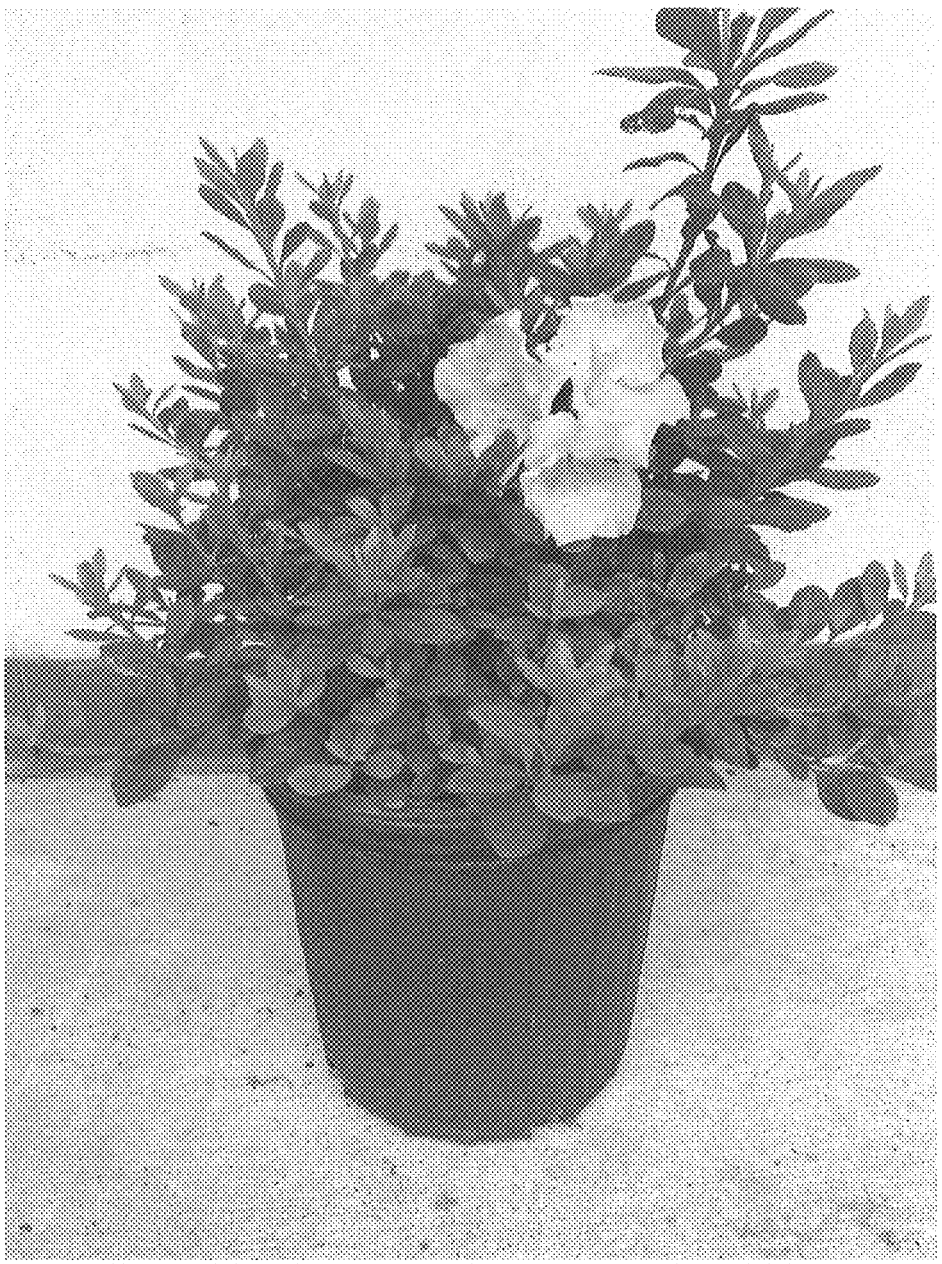
FIG. 1 illustrates a side view of the overall growth and flowering habit of the new variety.
Figure 2:
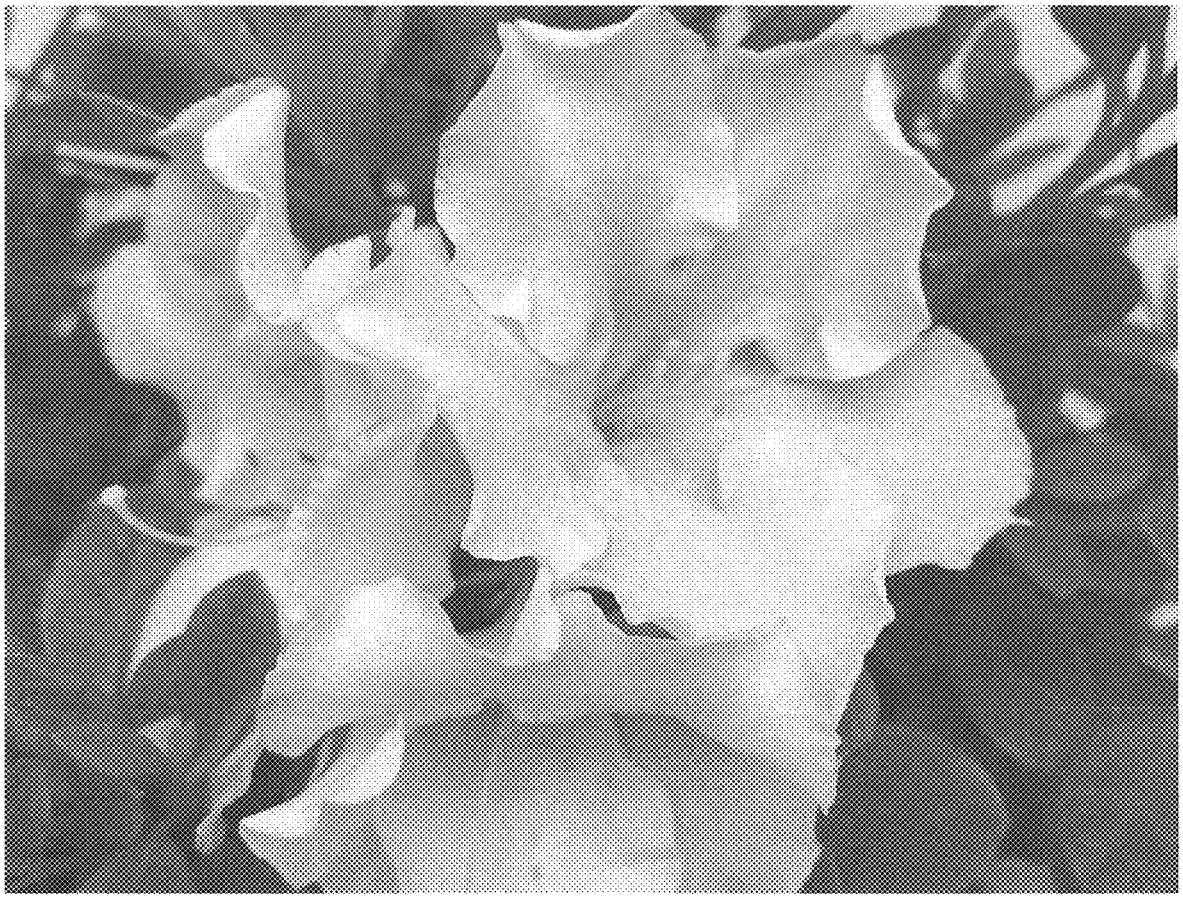
FIG. 2 illustrates a specimen of a flower—close-up view.

The chart used in the identification of the colors is that of The Royal Horticultural Society (The R.H.S. Colour Chart, 2015 edition), London, England. The terminology which precedes reference to the chart has been added to indicate the corresponding color in more common terms. The description is based on the observation of specimens of the new variety during July 2021 under natural light conditions in Cochranville, Pa. Measurements and numerical values represent averages of typical plants.

Botanical classification: *Rhododendron* hybrid cultivar Lazamorwhi.

Commercial classification: Azalea Plant.

Plant:

*Growth habit and general appearance*.—Moderately vigorous, mounding, globose, upright growth habit.

*Height*.—Approximately 23.0 cm from soil level to top of plant plane.

*Width*.—Approximately 35.0 cm.

Branches:

*Branching characteristics*.—Freely branching; pinching enhances branching; approximately 10 primary branches from center of plant, angled approximately 75 degrees from center of plant; each primary branch has 4 to 10 lateral branches.

*Primary branches*.—Strength: very strong, difficult to break. — length: approximately 13.0 to 15.0 cm. — diameter: approximately 5.0 mm. — color: commonly near Yellow-Green Group N145A, with age, covered with a thin bark like layer colored near Grey-Brown Group N199A. — texture: young growth hirsute, hairs, approximately 1.5 mm long, colored near Yellow-Green Group 145D; older growth is scaly, hirsute, hair color near White Group 155D.

*Secondary branches*.—Strength: very strong, flexible. — number of lateral branches: approximately 4 to 10 per primary branch. — length: approximately 14.0 cm. — diameter: approximately 5.0 mm. — color: commonly near Yellow-Green Group N144A. — texture: hirsute. — internode length: between 8.0 mm and 4.0 cm.

Foliage:

*Fragrance*.—None detected.

*Form*.—Simple.

*Arrangement*.—Alternate.

*Leaves*.—Shape: elliptic. — margin: entire. — apex: acute. — base: broad attenuate. — venation pattern: pinnate. — length of mature leaf: approximately 3.5 cm. — width of mature leaf: approximately 2.8 cm. — texture of upper surface: highly pubescent, hairs appressed. — texture of lower surface: pubescent, more hairs present along main vein and margin. — color of upper surface of young foliage: commonly near Yellow-Green Group 144A with indistinguishable venation. — color of lower surface of young foliage: commonly near Yellow-Green Group 146D with indistinguishable venation. — color of upper surface of mature foliage: commonly near Green Group 137A with venation of near Yellow-Green Group 153D. — color of lower surface of mature foliage: commonly near Green Group 138A with venation of near Yellow-Green Group 151A.

*Petiole*.—Length: approximately 8.0 cm. — diameter: approximately 3.0 mm. — color on upper and lower surfaces: commonly near Yellow-Green Group N144C.

Flowers:

*Flowering season*.—Flowers in spring and continues to produce flowers throughout Summer and Fall; flowering ends with the onset of frost.

*Lastingness of individual inflorescence on the plant*.—Approximately one week.

*Flower arrangement*.—Axillary clusters of perfect, open funnel shaped individual flowers; typically, 4 to 10 flowers per cluster.

*Bud just before opening*.—Shape: elliptic. — length: approximately 3.0 cm. — diameter: approximately 1.5 cm. — color: commonly near White Group 155A

*Inflorescence*.—Height: approximately 11.0 cm. — diameter: approximately 9.5 cm.

*Flowers*.—Length: approximately 6.0 cm. — diameter: approximately 8.0 cm. — facing direction: outwardly and upwardly facing. — persistent or self-cleaning: petals self-cleaning. fragrance: none. — flower tube length: approximately 2.5 cm. — flower tube width at widest point: approximately 2.5 cm. — flower tube width at narrowest point: approximately 1.2 cm.

*Petals*.—Unfused petal segment length: approximately 2.8 cm. — unfused petal segment width: approximately 2.0 cm. — apex: retuse. — shape of petal:

unfused portion, obovate. — petal margin: entire with ruffled aspect along margin. — petal arrangement: approximately ⅓ fused from base. — petal number: 5. — petal texture: smooth. — color upper surface at first opening: commonly near White Group 155A. — color under surface at first opening: commonly near White Group 155A. — color inner surface at maturity: commonly near White Group 155A. — color outer surface at maturity: commonly near White Group 155A. — color upper surface at fading: commonly near White Group 155A.

*Sepals*.—Quantity: commonly 5. — shape: narrow deltate. — margin: entire. — apex: acute. — base: fused. — length: approximately 7.0 mm. — width: approximately 4.0 mm. — texture: highly pubescent. — color of inner surface: commonly near Yellow-Green Group 145B. — color of outer surface: commonly near Yellow-Green Group 145A.

*Peduncle*.—Strength: strong. — shape: rounded. — aspect: straight to very slightly curved. — angle of attachment: approximately 45° from stem. — length: approximately 1.0 cm. — diameter: approximately 2.0 mm. — texture: densely pubescent. — color: commonly near Yellow-Green Group 145B.

*Reproductive organs*.—Stamen: quantity per flower is approximately 6; length is approximately 1.5 cm, width is approximately 1.0 mm, coloration is commonly near White Group N155D. — anther: length is approximately 3.0 mm and coloration is commonly near Greyed-Orange Group 163A. — pollen: not observed to date. — pistil: number is 1 and length is approximately 4.0 cm. — styles: length is approximately 4.0 cm, coloration is commonly near White Group N155D. — stigmas: globular and coloration is commonly near Yellow Group 2B. — ovary: sericeous texture; diameter is approximately 3.0 mm; coloration is commonly near Yellow-Green Group 144B; hairs colored commonly near White Group N155D.

*Seed and fruit production*.—Neither seed nor fruit production has been observed.

Development:

*Commercial crop time*.—Approximately one year from a rooted cutting to finish in a 3-gallon container.

*USDA hardiness zone*.—Zone 7 (0° F. to 10° F.).

*Disease and pest resistance*.—Not been observed.

The new 'Lazamorwhi' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Azalea plant named 'Lazamorwhi' characterized by the following combination of characteristics:

(a) forms solid, white colored single inflorescences, (b) exhibits medium-green colored foliage, and (c) provides moderately vigorous, mounding, globose, upright growth habit;

substantially as herein shown and described.

* * * * *